United States Patent
Shrader et al.

[11] Patent Number: 5,925,972
[45] Date of Patent: Jul. 20, 1999

[54] MULTIPLE ELEMENT PARTICLE SENSOR AND SIGNAL PROCESSING ELECTRONICS

[75] Inventors: Eric J. Shrader, Belmont; Hugh F. Frohbach, Sunnyvale; Joseph S. Eckerle, Redwood City, all of Calif.; Ronald E. Pelrine, Silverthorne, Colo.; John P. Marlow, Menlo Park, Calif.; Yukihisa Takeuchi, Nishikamo-gun; Kazuyoshi Shibata, Nagoya, both of Japan

[73] Assignee: NGK Insulators, Ltd., Japan

[21] Appl. No.: 08/721,964

[22] Filed: Sep. 27, 1996

[51] Int. Cl.⁶ .................................................. H01L 41/113
[52] U.S. Cl. .......................................... 310/338; 310/319
[58] Field of Search ..................... 310/319, 324, 310/330–332, 338

[56] References Cited

U.S. PATENT DOCUMENTS

| | | | |
|---|---|---|---|
| 3,715,911 | 2/1973 | Chuan | 73/23 |
| 3,816,773 | 6/1974 | Baldwin et al. | 310/338 |
| 3,868,667 | 2/1975 | Skujins | 340/272 |
| 4,214,484 | 7/1980 | Abts | 73/632 |
| 4,217,781 | 8/1980 | Abts | 73/632 |
| 4,531,267 | 7/1985 | Royer | 29/25.35 |
| 4,841,775 | 6/1989 | Ikeda et al. | 73/704 |
| 4,908,112 | 3/1990 | Pace | 204/299 R |
| 5,126,615 | 6/1992 | Takeuchi et al. | 310/330 |
| 5,210,455 | 5/1993 | Takeuchi et al. | 310/328 |
| 5,245,290 | 9/1993 | Cannon et al. | 324/457 |
| 5,281,888 | 1/1994 | Takeuchi et al. | 310/366 |
| 5,283,037 | 2/1994 | Baer et al. | 422/82.01 |
| 5,363,691 | 11/1994 | Gallagher | 73/32 A |
| 5,406,163 | 4/1995 | Carson et al. | 310/334 |
| 5,698,931 | 12/1997 | Shibata et al. | 310/338 |

FOREIGN PATENT DOCUMENTS

| | | | |
|---|---|---|---|
| 0455342 | 11/1991 | European Pat. Off. | H01L 41/09 |
| 0526048 | 2/1993 | European Pat. Off. | H01L 41/09 |
| 59-86916 | 5/1984 | Japan | H03H 19/17 |
| 60-72277 | 4/1985 | Japan | H01L 29/84 |
| 4-132921 | 5/1992 | Japan | G01L 9/12 |
| 2115222 | 9/1983 | United Kingdom | H01L 41/08 |
| 2249176 | 4/1992 | United Kingdom | G01N 15/02 |
| WO 93/09405 | 5/1993 | WIPO | G01F 1/74 |

OTHER PUBLICATIONS

"Electrostrictive Materials for Ultrasonic Probes in the $Pb(Mg_{1/3}Nb_{2/3})O_3$–$PbTiO_3$ System", Hiroshi Masuzawa et al., May 10, 1989, pp. 101–104, Proceedings of the 7th Meeting on Ferroelectric Materials and Their Applications, Kyoto 1989, Japanese Journal of Applied Physics, vol., #1989, Supplement 28–2.

Primary Examiner—Thomas M. Dougherty
Attorney, Agent, or Firm—Parkhurst & Wendel

[57] ABSTRACT

A sensor device adapted to detect at least one of a particle and a bubble in a fluid, includes a fluid nozzle defining a center of fluid flow; and a plurality of sensor elements for converting an impact of one of a particle and a bubble into an electrical signal, wherein a first sensor element is arranged closer to the center of fluid flow than a second sensor element. The sensor device includes a number of diaphragm sensor elements each having a sufficiently small mass for responding to a collision with the particle, and an apparatus for converting a vibration of the diaphragm portion into an electrical signal so as to detect the vibration. The multiple elements are arranged in the fluid flow stream such that different size particles will preferentially strike different elements.

13 Claims, 9 Drawing Sheets

MULTIPLE ELEMENT PARTICLE SENSOR AND SIGNAL PROCESSING ELECTRONICS

BACKGROUND OF THE INVENTION AND RELATED ART STATEMENT

The present invention relates to a sensor element and a particle sensor having a sensor element with multiple sensing surfaces. The sensor element includes a piezoelectric film for detecting particles in a fluid. The multiple sensing surfaces allow the average size of particles in a fluid flow to be measured.

When fluid, which is liquid or gas, contains solid particles, it is sometimes necessary to detect the presence of the particles as well as the particle size. Particularly, when the particles are undesirably present in fluid impeding the function of the fluid, it becomes important to detect the particles and also to determine relative size of the particles and to discriminate from bubbles or other non-particle signals.

For instance, an internal combustion engine, such as an engine for a car or an engine for a heavy machine, uses gasoline or diesel fuel as its power source. These internal combustion engines employ a lubricant to reduce friction drag and abrasion on rotating and sliding surfaces of the engine. In an internal combustion engine, particles such as metal powder generated by abrasion may mix with the lubricant so as to accelerate abrasion of the rotating or sliding surfaces. Particles in the lubricant are generally removed by a filter such as an oil filter. The conditions of a lubricant can be monitored in more detail by detection and size measurement of particles in the lubricant. Size measurement of the particles in the fluid is important because wear rates can be related to the size of the particles causing the wear. Therefore more particles of a size that do not cause wear can be tolerated than particles of a size that do cause wear.

One conventional method used to detect particles in fluid employs a pair of electrodes which are arranged with a gap of predetermined size therebetween, and electric resistance between the electrodes is monitored. In this method, when metal particles come in contact with both of the electrodes, the electrical resistance between the electrodes decreases, thus detecting the particle. However, this method cannot detect particles smaller than the gap between the electrodes, and also cannot detect electrically insulating particles.

In another method, a magnetic field is generated in a detecting unit by an electric magnet or the like so as to detect the amount of particles such as metal particles accumulated on the detector. However, this method cannot detect non-ferromagnetic particles, and thus its accuracy is limited.

In still another method, the amount of particles in the fluid is correlated with the transmittance of light through the fluid so as to detect the amount of particles in the fluid. However, the transmittance of the fluid is not always constant, and dirt on a window for incident light or a window for transmitted light adversely affects measurement accuracy, which limits durability of the sensor.

U.S. patent application Ser. No. 08/443,464 discloses a particle sensor including a piezoelectric film mounted onto a vibrating portion, and the piezoelectric film converts vibration caused by particles into an electric signal. The subject matter of U.S. patent application Ser. No. 08/443,464 is hereby incorporated by reference thereto.

However, the sensor element may generate an electric signal upon impact of a bubble in the fluid, causing an error. Therefore, it is desired to discriminate electric signals induced by solid particles from electric signals induced by bubbles.

Moreover, in some applications, it is desired to detect bubbles in the fluid. For example, the working fluid in a transmission is preferably bubble-free because bubbles reduce the effectiveness of the fluid for power transmission. Monitoring the presence of bubbles assures smooth and efficient operation of the transmittion.

SUMMARY OF THE INVENTION

The present invention aims at solving the problems described above and providing a low cost sensor element and particle sensor having excellent detection accuracy, particle sizing capability, and durability.

One object of the present invention is to provide a sensor element for detecting a foreign solid particle in a fluid and measuring the average size of particles in the fluid. The sensor element includes a number of diaphragm sensor elements each having a sufficiently small mass for responding to a collision with a solid particle, and an apparatus for converting a vibration of the diaphragm portion into an electrical signal so as to detect the vibration. The multiple elements are arranged in the fluid flow stream such that different size particles will preferentially strike different elements. In particular, a first element is aligned with a center of the fluid flow stream, while a second and any additional elements are offset from the center of the fluid flow stream.

Another object of the present invention is to provide a multiple element sensor with improved reliability. Reliability is improved by using multiple elements. If any of the individual elements becomes damaged or worn, the remainder of the elements continue to function and the sensor as a whole continues to function although with reduced accuracy.

Another object of the present invention is to provide a sensor element including: a detecting unit including multiple elements each consisting of a piezoelectric film consisting essentially of a first ceramic material, a first electrode coated onto at least a portion of the outer surface of the piezoelectric film, and a second electrode coated onto at least a portion of the inner surface of the piezoelectric film; a vibrating portion consisting essentially of a second ceramic material, the detecting unit being placed on the vibrating portion so that the second electrode contacts at least a portion of the vibrating portion; and a fixed portion for holding the vibrating portion such that the vibrating portion may vibrate; wherein the detecting unit and/or the vibrating portion make contact with and are vibrated by solid particles in a fluid and the piezoelectric film converts the vibration into an electrical signal. The vibrating portion of each sensor element vibrates only when it is struck by a particle, thus providing means for detecting which element was struck.

The vibrating portion and the fixed portion may be portions of a ceramic substrate having a unitary structure, and the ceramic substrate is preferably formed with a cavity so that the vibrating portion has a plate or diaphragm shape of small thickness.

The first ceramic material preferably comprises at least one material selected from the group consisting of lead zirconate, lead magnesium niobate, lead nickel niobate, lead zinc niobate, lead manganese niobate, lead antimony stanate, lead titanate, and barium titanate. The fluid is preferably a lubricant. The piezoelectric film preferably has a thickness ranging from 1 to 100 micrometers, and the vibrating portion preferably has a thickness ranging from 1 to 100 micrometers. The vibrating portion preferably comprises stabilized zirconium oxide.

Still another object of the present invention provides a particle sensor including: (a) a set of sensor elements each including: a detecting unit including a piezoelectric film consisting essentially of a first ceramic material, a first electrode coated onto at least a portion of the outer surface of said piezoelectric film, and a second electrode coated onto at least a portion of the inner surface of the piezoelectric film; a vibrating porion consisting essentially of a second ceramic material, the detecting unit being placed on the vibrating portion so that the second electrode contacts at least a portion of the vibrating portion; and a fixed portion for holding the vibrating portion such that the vibrating portion may vibrate; wherein when the detecting unit and/or said vibrating portion makes contact with and is vibrated by solid particles in the fluid, the piezoelectric film converts the vibration into an electrical signal; and (b) a protection cover covering the detecting unit.

Still another object of the present invention provides an electronic circuit for elimination of signals caused by bubbles in the fluid exciting the sensor. The electronic circuit includes a first amplifier, a first bandpass filter, a time delay generator, a second bandpass filter, and a signal gate. In particular, the electronic circuit includes an amplifier for amplifying the magnitude of an electrical signal, an envelope-detector means for forming an approximation to an envelope of the high frequency component of the electrical signal, rise-time-verifier means for detecting a rise time of the electrical signal so as to compare the rise time against a first predetermined value, wherein when the rise a time is shorter than the first predetermined value, said rise-time-verifier means outputs the electrical signal, and detecting means for detecting presence of a low-frequency component of the electrical signal during a predetermined time interval, whereby when the low-frequency component is present, the electrical signal is induced by a bubble.

Additionally, the present invention provides a method for discriminating between electrical signal induced by a particle in a fluid and an electrical signals induced by a bubble therein.

DETAILED DESCRIPTION OF THE INVENTION

Figure 1:
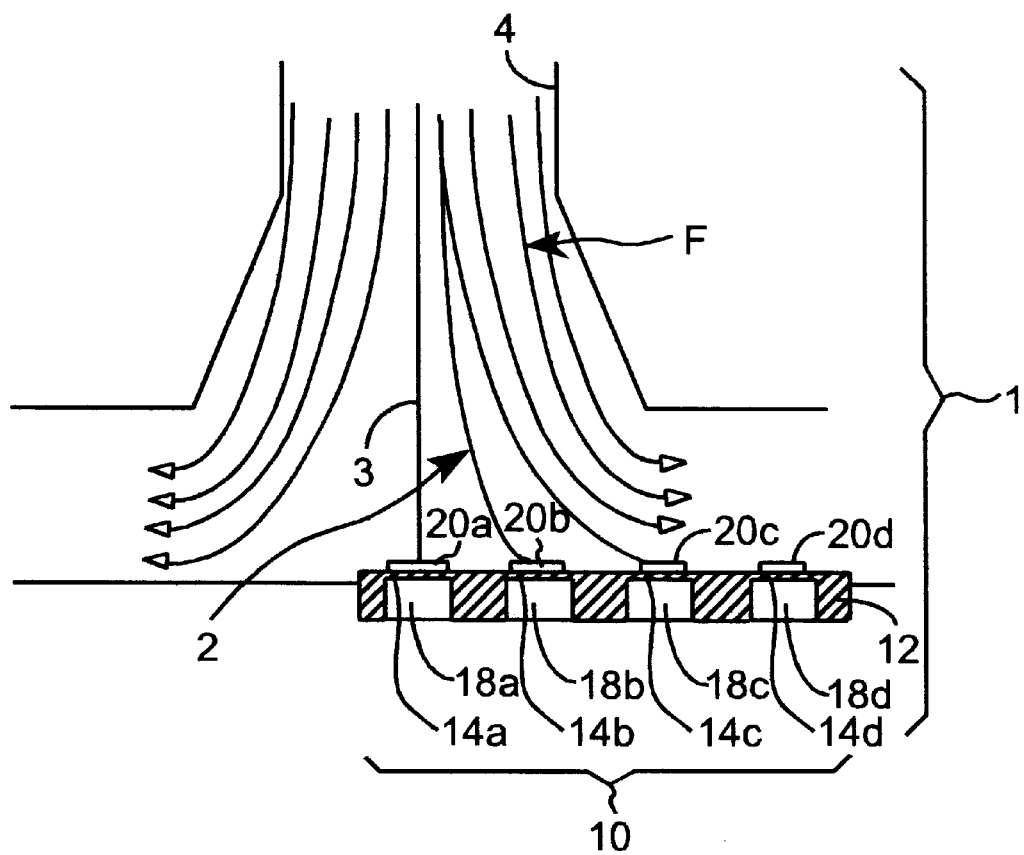
FIG. 1 is a cross-sectional view of an exemplary sensor geometry.

FIG. 1 shows an exemplary sensor geometry with a four element sensor 1. Fluid flows in a pipe 4 in the direction of arrows "F". A particle trajectory 2 is shown striking element 20b (the second element from the center streamline 3). The number of particles striking each element can be used to calculate the average particle size of the particles in the fluid and therefore estimate the quality of the fluid as a lubricant.

In FIG. 1, a device 10 includes a ceramic substrate 12 formed of depressions 18a, 18b, 18c, 18d to give vibrating portions 14a, 14b, 14c, 14d. A plurality of detecting units 20a, 20b, 20c, 20d are mounted onto the vibrating portions 14a, 14b, 14c, 14d of the ceramic substrate 12, opposite to the depressions 18a, 18b, 18c, 18d. However, the detecting units may be arranged in the depressions 18a, 18b, 18c, 18d. A sensor element includes one of the vibrating portions 14a, 14b, 14c, 14d and its corresponding detecting unit. Each of the detecting units 20a, 20b, 20c, 20d includes a piezoelectric film for converting vibration into an electrical signal.

In FIG. 1, the device 10 is arranged eccentric to the center 3 of the flow stream in fluid formed by an entrance 4. Each of the detecting units 20a, 20b, 20c, 20d is impacted by particles that follow a different path to the device 10. The path that a particular particle follows is determined by the particle starting point, the particle mass, the fluid properties and the flow velocity.

In FIG. 1, the detecting unit 20a is arranged on the center 3 of the flow stream so that particles of all the sizes strike the detecting unit 20a. A larger particle tends to strike the detecting unit 20b, being closer to the center 3 of the flow stream, whereas a smaller particle tends to strike the detecting unit 20d, being far from the center 3 of the flow stream.

When the electrical signals from all of the detecting units 20a, 20b, 20c. 20d are added, the overall electrical signal represents particles of all sizes striking the detecting units 20a, 20b, 20c, 20d. On the other hand, when electrical signals of each of the detecting units 20a, 20b, 20c, 20d are separately processed, the distribution of particle sizes is obtained.

Figure 2:
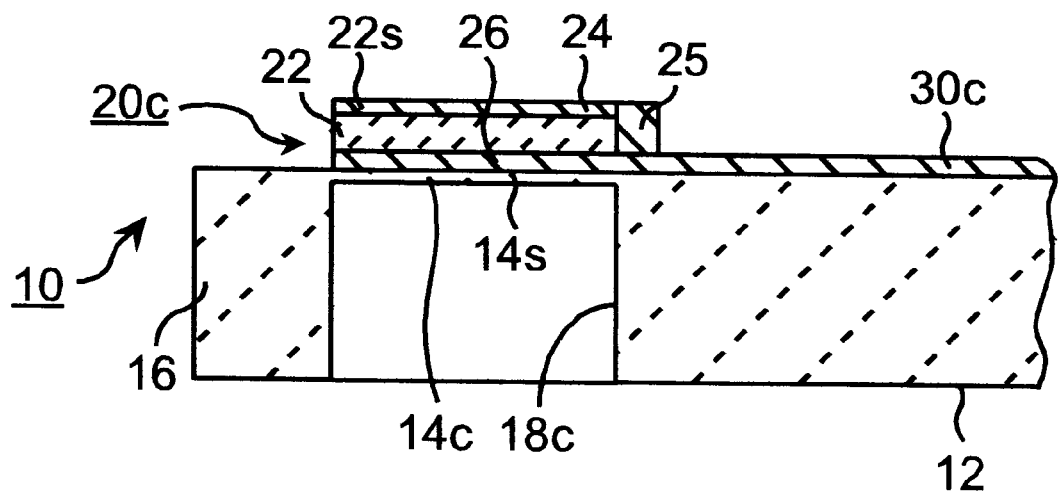
FIG. 2 is an enlarged partial cross-sectional view of a sensor element according to the present invention, which is also a cross-sectional view of FIG. 4 at the line II—II.
Figure 3:
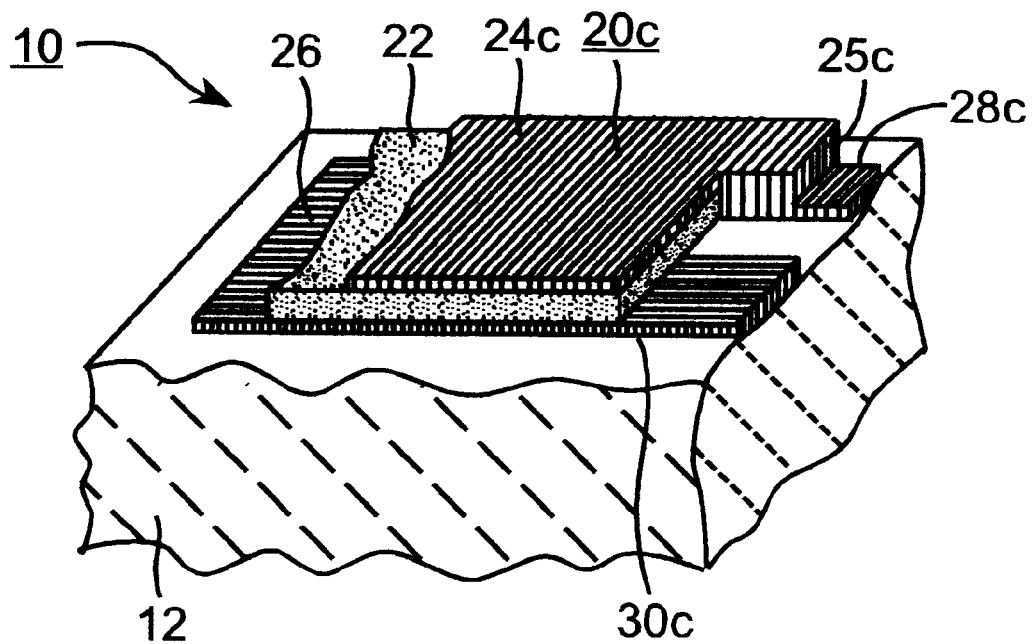
FIG. 3 is a partial perspective view of sensor element of FIG. 2.
Figure 4:
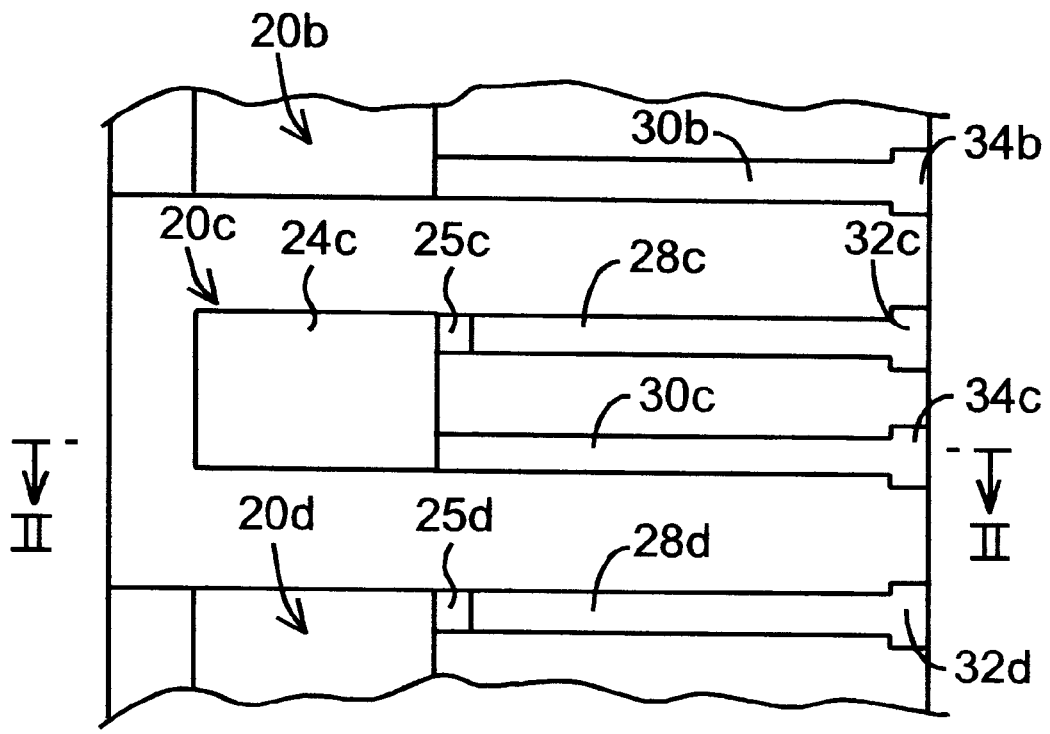
FIG. 4 is a partial top view of sensor element of FIG. 2.

FIG. 2 is an enlarged partial cross-sectional view of device 10, which is also a cross-sectional view at line B–B' of FIG. 4. FIG. 2 is representative of the sensor elements, and illustrates a vibrating portion 14c and its corresponding detecting unit 20c. The other vibrating portions and detecting units may be the same in terms of structure, shape, materials and formation techniques. FIG. 3 is a partial perspective view of the device 10 shown in FIG. 2, wherein a portion of a piezoelectric film 22 and a portion of the upper electrode 24c are omitted for clarity. FIG. 4 is a partial top view of the device 10 shown in FIG. 2.

In reference to FIGS. 2 and 3, the device 10 has a substrate 12 and a detecting unit 20c placed on a vibrating portion 14c. The substrate 12 has a monolithic structure. The vibrating portion 14c and a fixing portion 16 are portions of the substrate 12. The detecting unit 20c is placed on the upper side of the vibrating portion 14c. The fixing portion 16 is positioned at the lower side of the vibrating portion 14c so as to surround the vibrating portion 14c. However, it is not necessary in the present invention that the vibrating portion and the fixing portion be portions of the structure. For example, a metal fixing portion may be secured to an independent vibrating portion made of ceramic. When the fixing portion is made of metal, the surface of the vibrating portion to be connected to the fixing portion may be metallized so that the metallized layer may be bonded to the fixing portion by soldering. Alternatively, the vibrating portion may be pressed into a recess in the fixing portion. A metal such as stainless steel or iron may be employed for the fixing portion.

The substrate 12 is formed with a depression 18c so that the vibrating portion 14c has the shape of a thin plate or diaphragm. The detecting unit 20c is placed so as to correspond to the position of the depression 18c. However, the present invention is not limited to a depression. For example, a closed cavity may be formed to provide a diaphragm.

The vibrating portion 14c vibrates with the detecting unit 20c vertically, i.e., in the direction toward the detecting unit 20c or toward the cavity 18c when the sensor element 10 detects a particle. Preferably, the vibrating portion 14c is plate-shaped because this shape is suitable for vibration. In this case, the thickness of the plate is preferably 1–100 $\mu$m, more preferably, 3–50 $\mu$m, furthermore preferably, 5–20 $\mu$m.

The vibrating portion 14c is preferably made of a material able to withstand high temperatures so as to prevent thermal degeneration of the vibrating portion. This is because the detecting unit 20c may be placed directly on the vibrating portion 14c without any material (such as an organic adhesive which cannot withstand high temperatures) therebetween. In such a case, the vibrating portion 14c also should not be damaged by the high temperature used when the piezoelectric film 22 is formed. When the sensor element is used for a lubricant such as oil, it sometimes happens that the vibrating portion contacts an organic solvent contained in the lubricant or that the lubricant changes to be acidic or basic. Therefore, the vibrating portion is preferably made of a chemically stable material.

The vibrating portion 14c is preferably made of an electric insulator because the second electrode covering at least a part of the vibrating portion 14c, leads connected to the first electrode and to the second electrode, lead terminals, and the like are all electrically conductive. Therefore, the vibrating portion 14c may be made of a metal having good high temperature properties, which is covered with a ceramic such as glass. Most preferably, the vibrating portion 14c is made of ceramic. For example, zirconium oxide that is stabilized, aluminum oxide, magnesium oxide, mullite, aluminum nitride, silicon nitride, glass, or the like can be suitably used for the vibrating portion. Zirconium oxide that is stabilized is preferable because it has high mechanical strength and high toughness even if the vibrating portion is thin, and low chemical reactivity with the piezoelectric film and electrodes, etc.

Zirconium oxide that is stabilized includes stabilized zirconia and partially stabilized zirconia. Zirconium oxide that is stabilized does not undergo a phase transition since it has a cubic crystal structure, for example. On the other hand, zirconium oxide that is not stabilized undergoes a phase change between a monoclinic structure and a tetragonal structure at around 1000° C. This phase change may generate cracks. Zirconium oxide that is stabilized contains 1–30% by mole of calcium oxide, magnesium oxide, yttrium oxide, scandium oxide, ytterbium oxide, cerium oxide, or a stabilizer such as a rare earth metal oxide. Preferably, the stabilizer contains yttrium oxide so as to enhance mechanical strength of the vibrating portion. The amount of yttrium oxide contained in the stabilizer is preferably 1.5–6% by mole, more preferably 2–4% by mole. Further, the main crystalline phase may belong to the tetragonal system or a mixture of the tetragonal system and the cubic system.

The ceramic composing the vibrating portion 14c preferably contains 0.5–5% by weight of silicon oxide, more preferably 1–3% by weight, because silicon oxide prevents an excessive reaction between the vibrating portion 14c and the detecting unit 20c upon forming the detecting unit 20c by thermal treatment.

When the vibrating portion 14c consists of ceramic, it is composed of numerous gains. The average diameter of the grains is preferably 0.05–2 $\mu$m, more preferably 0.1–1 $\mu$m.

The fixing portion 16 fixes at least a part of the vibrating portion 14c or at least a part of the circumference of the vibrating portion 14c. In the mode of operation shown in FIG. 1, the fixing portion preferably consists of ceramic. The ceramic material for the fixing portion 16 may be the same as that of the vibrating portion, or may be different. Zirconium oxide that is stabilized, mullite, aluminum oxide, magnesium oxide, aluminum nitride, silicon nitride, glass, or the like, is suitable for the ceramic composing the fixing portion as well as for the vibrating portion 14c.

The shape of depression 18c is not limited. A horizontal or vertical cross section of the depression may be, for example, a circle, an oval, a polygon including a square and a rectangle, or a complex shape formed by combining some of these shapes. However, when the shape is a polygon or the like, the corners are preferably rounded so as to remove sharp edges.

The detecting unit 20c includes a piezoelectric film 22, the first electrode 24 covering at least a part of the outer surface 22s of the piezoelectric film 22, and the second electrode 26 covering at least a part of the inner surface 22t of the piezoelectric film. The second electrode 26 covers at least a part of the outer surface 14s of the vibrating portion 14c.

The piezoelectric film 22 microscopically generates dielectric polarization and macroscopically outputs an electric signal, for example, electric charge or voltage, corresponding to stress. In this case, the piezoelectric film preferably experiences flexing displacement in the direction of its thickness. When particles contact with the first electrode and/or the vibrating portion, the piezoelectric film 22 vibrates with the vibrating portion 14c. This vibration gives rise to stresses applied to the piezoelectric film 22.

The piezoelectric film preferably has a thickness of 1–100 $\mu$m, more preferably 5–50 $\mu$m, furthermore preferably 5–30 $\mu$m.

A piezoelectric ceramic can be suitably used for the piezoelectric film. The piezoelectric film may be a ceramic having electrostriction or a ceramic having ferroelectricity. Further, both a material which requires a treatment for polarization and a material which does not require a treatment for polarization can serve the purpose.

The ceramic for a piezoelectric film may contain, for example, lead zirconate, lead magnesium niobate, lead nickel niobate, lead zinc niobate, lead manganese niobate, lead antimony stanate, lead titanate, barium titanate, or a combination thereof. The ceramic may contain not less than 50% by weight of a compound consisting of these as a main component. A ceramic containing lead zirconate can be preferably used. Further, oxides of lanthanum, calcium, strontium, molybdenum, tungsten, barium, niobium, zinc, nickel, manganese, or the like; a combination thereof; or other compounds may be suitably added to the above-described ceramic. For example, it is preferable to employ ceramic containing a component consisting of lead magnesium niobate, lead zirconate, and lead titanate as a main component, and further containing lanthanum and strontium.

The piezoelectric film may be dense or it may be porous. When the piezoelectric film is porous, the porosity is preferably 40% or less.

The piezoelectric film may be consist of one layer or may be a laminated film consisting of at least two layers. When the piezoelectric film has a laminated structure, each of the layers may be placed horizontally or may be placed vertically.

It is also possible to place a detecting unit not only on one side of the vibrating portion but also on both sides of the vibrating portion.

In FIG. 3, the first electrode 24c and the second electrode 26 output an electric signal from the piezoelectric film 22 via a lead 28c and a lead 30c to a terminal pad 32c and a terminal pad 34c (see also FIG. 4). The first electrode 24c is connected to the lead 28c by a connecting portion 25c. The connecting portion 25c contacts the piezoelectric film 22 and does not contact the second electrode 26 and the lead 30c. Note, the second electrode 26, the lead 28c, the lead 30c, the terminal pad 32c and the terminal pad 34c may be formed simultaneously by a method for forming a thin film, which will be described later.

Each of the first electrode and the second electrode has a suitable thickness depending on its use. However, it is preferably 0.1–50 μm.

It is preferable that the first electrode be solid at room temperature and composed of electrically conductive metals. For example, metals such as aluminum, titanium, chromium, iron, cobalt, nickel, copper, zinc, niobium, molybdenum, ruthenium, rhodium, silver, tin, tantalum, tungsten, iridium, platinum, gold, lead, or the like; or an alloy thereof may be used. Needless to say, the first electrode may contain these elements in any combination. A metal belonging to the platinum group such as platinum, rhodium, palladium, or an alloy containing these metals, such as silver-platinum, or platinum-palladium is suitably used for the main component of the material for the electrode. Copper, silver, and gold are more preferable because they have durability.

The second electrode preferably consists of a simple substance containing a metal having a high melting point, such as platinum, ruthenium, rhodium, palladium, iridium, titanium, chromium, molybdenum, tantalum, tungsten, nickel, cobalt; or an alloy thereof. Needless to say, the second electrode may contain these metals having a high melting point in any combination. A metal belonging to a platinum group such as platinum, rhodium, palladium, or an alloy containing these metals, such as silver-platinum or platinum-palladium is suitably used for the main component of the material for the electrode. A metal resistant to an oxidizing atmosphere at high temperatures is used for the second electrode because the second electrode is sometimes exposed to a high temperature during thermal treatment of the piezoelectric film.

A material suitably used for the second electrode may be a cermet containing a metal having a high melting point and a ceramic such as alumina, zirconium oxide, silicon oxide, or glass.

The shape of the substrate is not especially limited and is selected depending on its application. The shape of the substrate is preferably planar. However it may be cylindrical or tubular.

Figure 5:
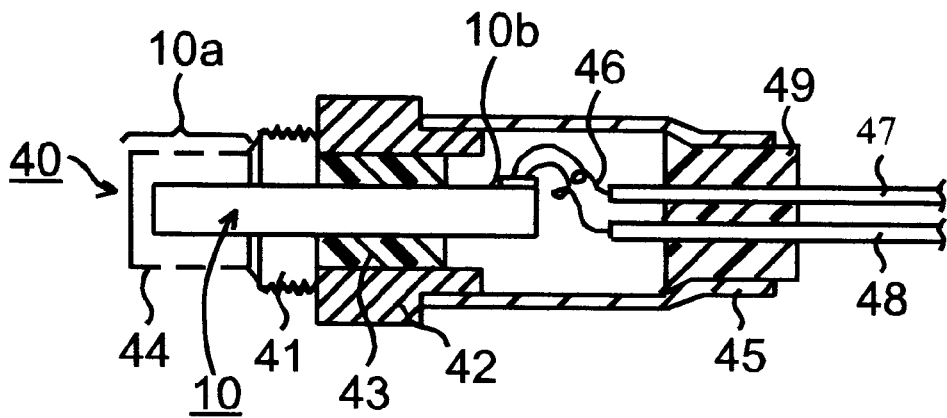
FIG. 5 is a cross-sectional view of a particle sensor of the present invention.

FIG. 5 is a cross-sectional view of a particle sensor 40 which includes the sensor element 10. The sensor element 10 can be attached to a wall (not shown) by a screw portion 41, and thereby the end portion 10a placed on the detecting unit 20 projects from the wall and contacts a fluid to be measured.

The screw portion 41 is connected to a housing 42. Alternatively, the screw portion 41 and the housing 42 may be combined into one piece. A shock-absorbing member 43 is installed inside the housing 42 against the sensor element 10.

The end portion 10a of the sensor element 10 is covered with a protecting cover 44. The protecting cover 44 has a plurality of throughholes so that fluid can flow into the protecting cover 44.

Since the other end portion 10b of the sensor element 10 is connected to wires 46, an electric signal present on the terminal pads 32 and 34 can be transmitted to the lines 47 and 48. The end portion 10b of the sensor element 10 and the wires 46 are inserted into a casing 45. An end of the casing 45 is sealed with an end portion member 49. The lines 47 and 48 pass through the end portion member 49.

A method of manufacturing a sensor element 10 of the present invention is hereinafter described.

Molded layers of green sheet or green tape are laminated by thermally pressing, and are then sintered to obtain an integrated substrate. For example, in the substrate 12 of FIG. 1, three layers of green sheets or green tapes are laminated. The second layer is formed in advance with a throughhole of a predetermined shape so as to form the cavities 18a–d. The layers may be formed by press molding, slip casting, injection molding, or the like. The cavities may be formed by machining such as cutting, grinding processing, laser machining, blanking by press working, or the like. It is not required that the layers have the same thickness. However, it is preferable that each of the layers has the same degree of shrinkage during sintering.

When the cavity is open (i.e., a depression), green sheets or green tapes may be molded so as to have a shape corresponding to the depression before being sintered. Alternatively, the cavity may be formed by machining after sintering.

A method for forming the detecting unit 20c on the ceramic vibrating portion 14c is now described. A piezoelectric body is formed by press molding in which a mold is employed, tape forming in which slurry is employed, or the like. Before sintering, the piezoelectric body is laminated on the vibrating portion of the substrate by thermal pressing. Then, this laminate is subjected to sintering to form a substrate and a piezoelectric body that are bonded together. This method requires that the electrode 26 be previously formed on the substrate by one of the methods of forming a film described later.

Though the sintering temperature of a piezoelectric film is suitably determined depending on the materials which compose the film, it is generally 800° C.–1400° C., preferably 1000° C.–1400° C. It is preferable that the piezoelectric film be sintered together with the presence of an evaporating source for the piezoelectric film material so as to control the composition of the piezoelectric film.

On the other hand, in a method for forming a film, the second electrode 26, the piezoelectric film 22c, and the first electrode 24c are laminated on the vibrating portion 14c in this order to form the detecting unit 20c. A method for forming a film is conventional in the art, for example, by thick film forming techniques such as screen printing, and dipping, and by thin film forming techniques such as ion beam, sputtering, vacuum deposition, ion plating, chemical vapor deposition (CVD), and plating. However, a method for forming a film is not limited to these methods.

The second electrode 26, the lead 28c, the lead 30c, the terminal pad 32c, and the terminal pad 34c, are simultaneously applied to the substrate by screen printing. Preferably, the piezoelectric film 22 is formed by screen printing, dipping, coating, or the like. These methods use paste or slurry which contains ceramic powders of the piezoelectric film material as a main component, and therefore the piezoelectric film 22 is formed on the substrate with the detecting unit 20c having excellent piezoelectric properties. Forming a piezoelectric film by one of these methods for forming films does not require any adhesive, and a detecting unit and a vibrating portion can be integrally connected. Therefore, such a method is particularly preferable in view of its excellent reliability, excellent reproducibility, and easy integration. The shape of such a film may be suitably patterned. A pattern may be formed by a method such as screen printing or photolithography or by removing unnecessary parts by machining such as laser machining, slicing or ultrasonication.

The shapes for the piezoelectric film, the first electrode, and the second electrode are not limited at all and any shape may be employed depending on its use. For example, they may be a polygon such as a triangle and a square, a curved shape such as a circle, an oval, and a torus, a comblike shape, a lattice, or a combination of these to form a special shape.

Each of films 22, 24c, and 26, which are formed in a shape on the substrate may be subjected to thermal treatment respectively whenever each film is formed, so that the film and substrate are integrated. Alternatively, the films may be subjected to thermal treatment simultaneously so as to integrally connect the films and the substrate, When the first electrode or the second electrode is formed by a method for forming a thin film, thermal treatment is not always necessary to integrate these electrodes.

Figure 6:
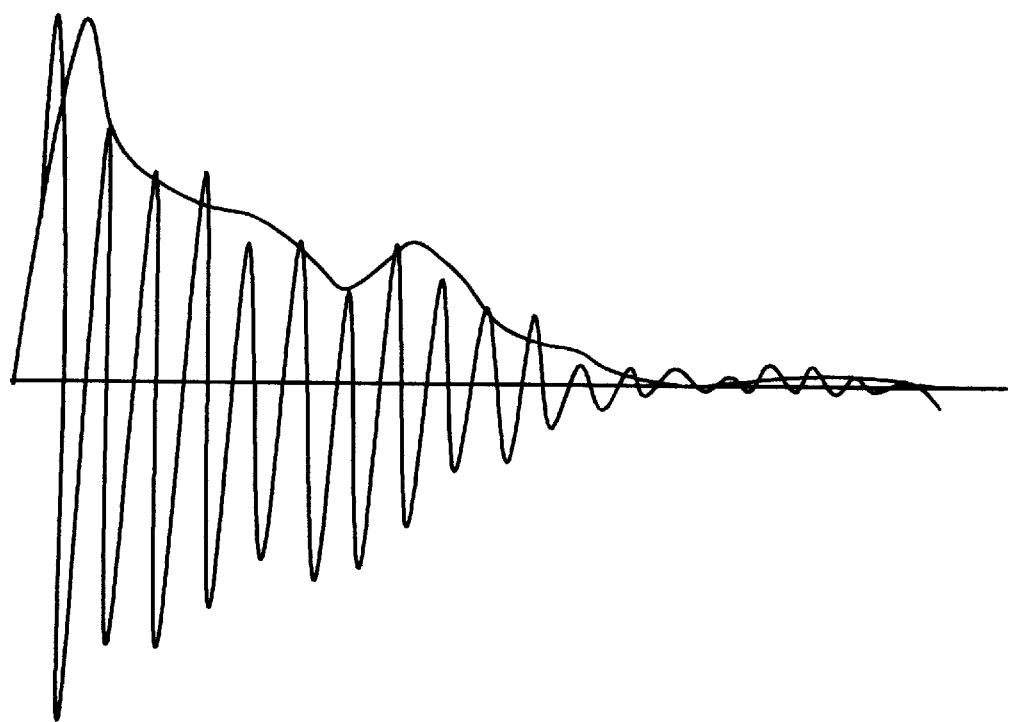
FIG. 6 is a sketch of typical responses of piezoelectric elements indicated qualitatively.
Figure 7:
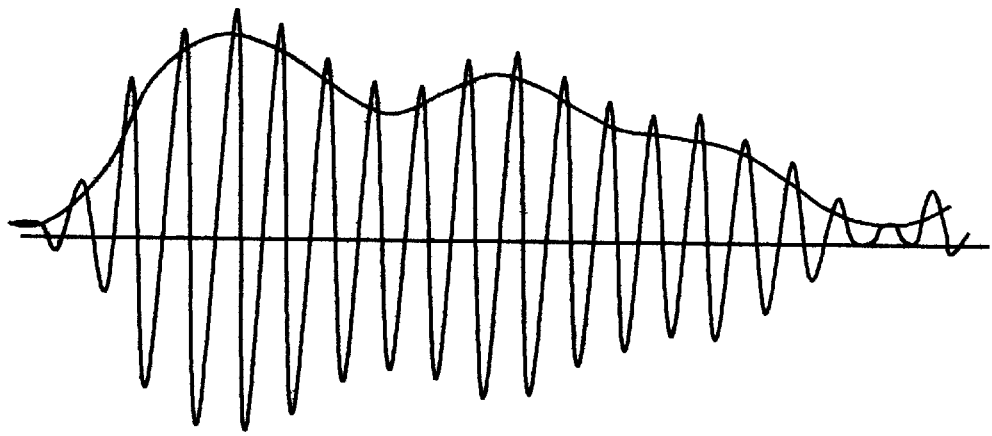
FIG. 7 is a sketch of typical responses of piezoelectric elements indicated qualitatively.
Figure 8:
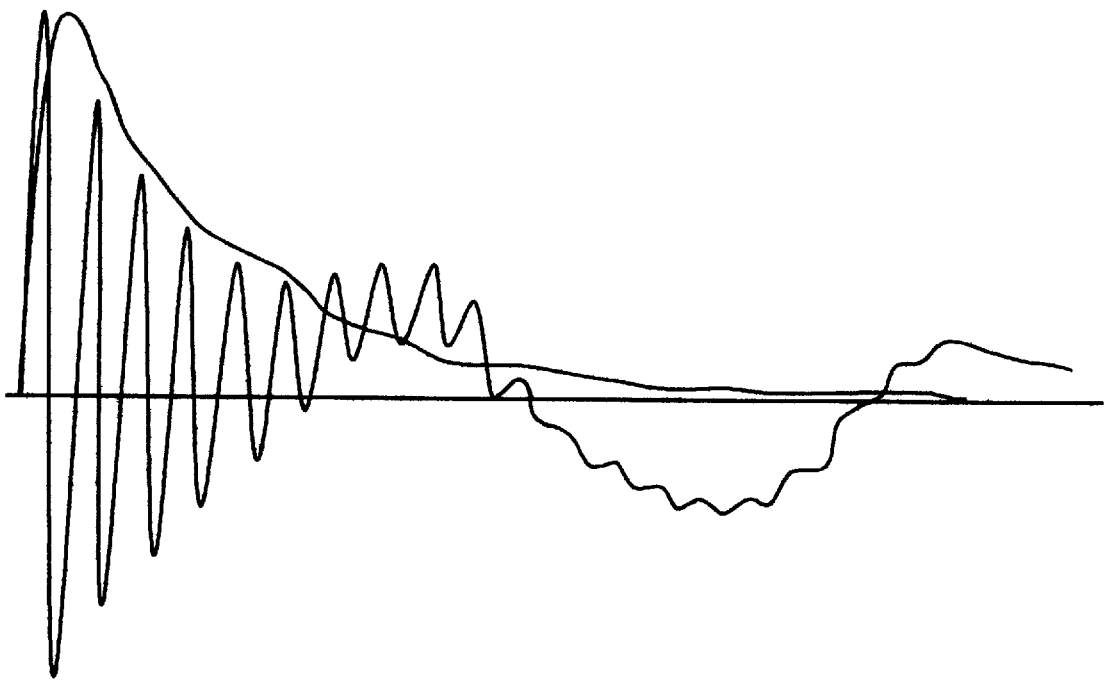
FIG. 8 is a sketch of typical responses of piezoelectric elements indicated qualitatively.

Typical responses from sensor elements are indicated qualitatively in the sketches of FIGS. 6, 7, and 8. The desired particle signal response with high frequency envelope is shown in FIG. 6. Specifically, FIG. 6 is typical of a strike from a foreign particle in oil. Two different types of undesirable spurious signals are shown in FIGS. 7 and 8. These spurious signals are probably caused by external sensor vibration or air bubbles in the fluid. It is the object of the electronics described below to discriminate between the first signal type and the other two types.

In accordance with the present invention, the particle sensor provides an output only when a signal like FIG. 6 is detected, and ignores signals typified by FIGS. 7 or 8.

The principal difference between the particle waveform of FIG. 6 and the bubble response in FIG. 8 is that the latter contains a low-frequency variation following the initial sudden high-frequency oscillation. Both waveshapes are nearly the same at the beginning, so the decision as to which type of signal has occurred cannot be made until a period of time has elapsed after the start of the signal.

Thus, the sequence of tasks that must be performed is: (1) to detect the start of a signal, (2) to wait a fixed period of time, (3) to sense the presence of lower frequencies, if any, in the signal during this period, and (4) if no low frequencies are sensed, to signal the presence of a particle.

In one embodiment of the present invention, these tasks are performed as follows:

When the start of a sharply rising oscillatory signal is detected a bistable flip-flop is set. Simultaneously a fixed-duration timer is started. If, while this timer is running, a low frequency component is sensed, then the flip-flop is cleared (reset). When the timer reaches its preset duration, the state of the flip-flop indicates whether or not to report the presence of a particle. If the flip-flop has remained set, then a particle is reported.

Spurious signals which have a slow build-up such as that of FIG. 7 are rejected by requiring that the bistable flip-flop be set only if the envelope of the signal reaches its first maximum in a short time. For this reason a circuit is included which rejects those signals that do not peak within a short time after onset, i.e., a short time after exceeding some preset threshold level. For example, to be reported as a particle, a signal must reach its peak amplitude in less than 8 $\mu$s after its arrival and have very little low frequency energy (below 50 kHz) within a 200 $\mu$s time period thereafter.

Figure 9:
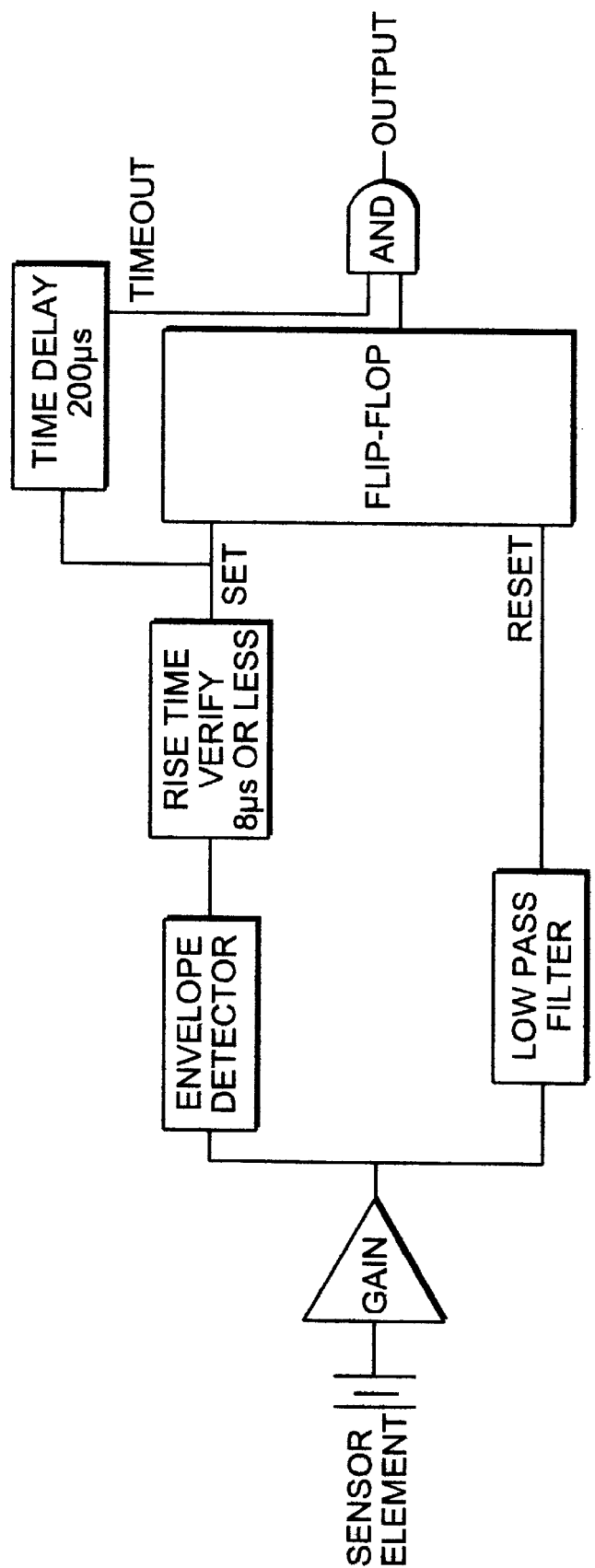
FIG. 9 is a block diagram of circuitry used to discriminate particle signals from spurious signals.

A block diagram of circuitry to implement these requirements is shown in FIG. 9. Schematic diagrams showing details of the blocks are shown in FIGS. 10, 11 and 12.

The block diagram of FIG. 9 shows the sequence of discrimination functions in pictorial form. Note that the output of the piezoelectric sensor after amplification is applied simultaneously to both an envelope detector and a low-pass filter.

The signal from the envelope detector is applied to a rise-time verifier that responds only to signals that peak within 8 $\mu$s after onset. The output of the verifier sets a flip-flop and initiates a 200 $\mu$s delay timer. If, while the timer is running, a low-frequency signal is present in the piezoelectric signal, then the signal will pass through the low-pass filter and reset the flip-flop. Otherwise the flip-flop remains set. Thus, when the timer runs out, the state of the flip-flop indicates whether a waveform like FIG. 6 or like FIG. 8 was detected. The presence of a particle is reported by the logical combination of both the timeout pulse and the flip-flop being set.

Figure 10:
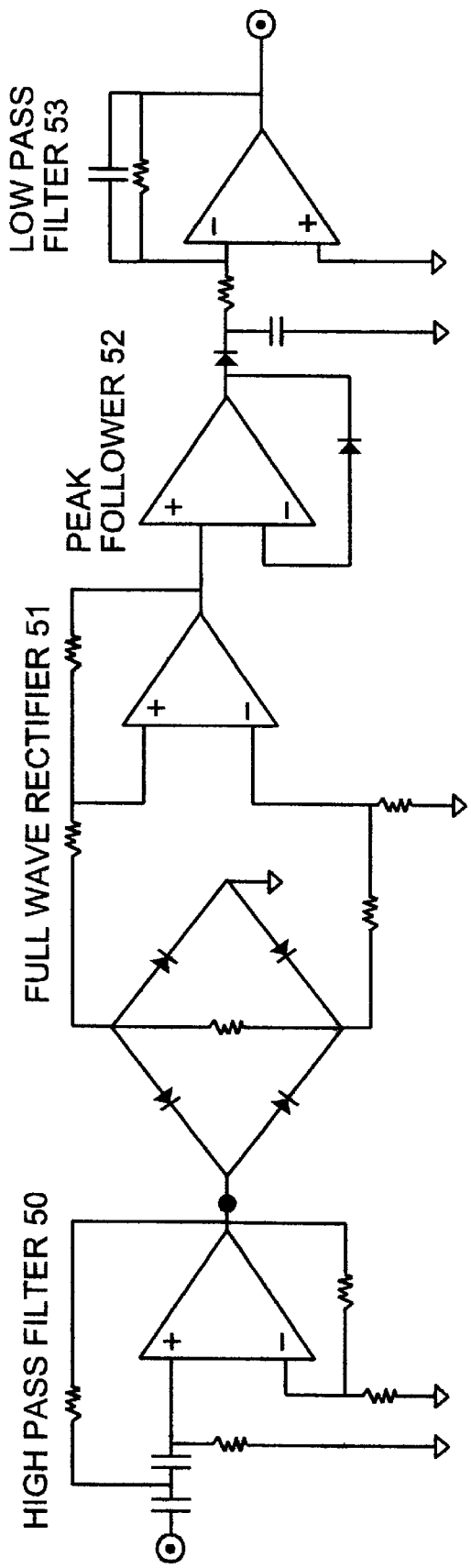
FIG. 10 is a schematic diagram showing details of the blocks in FIG. 9.
Figure 11:
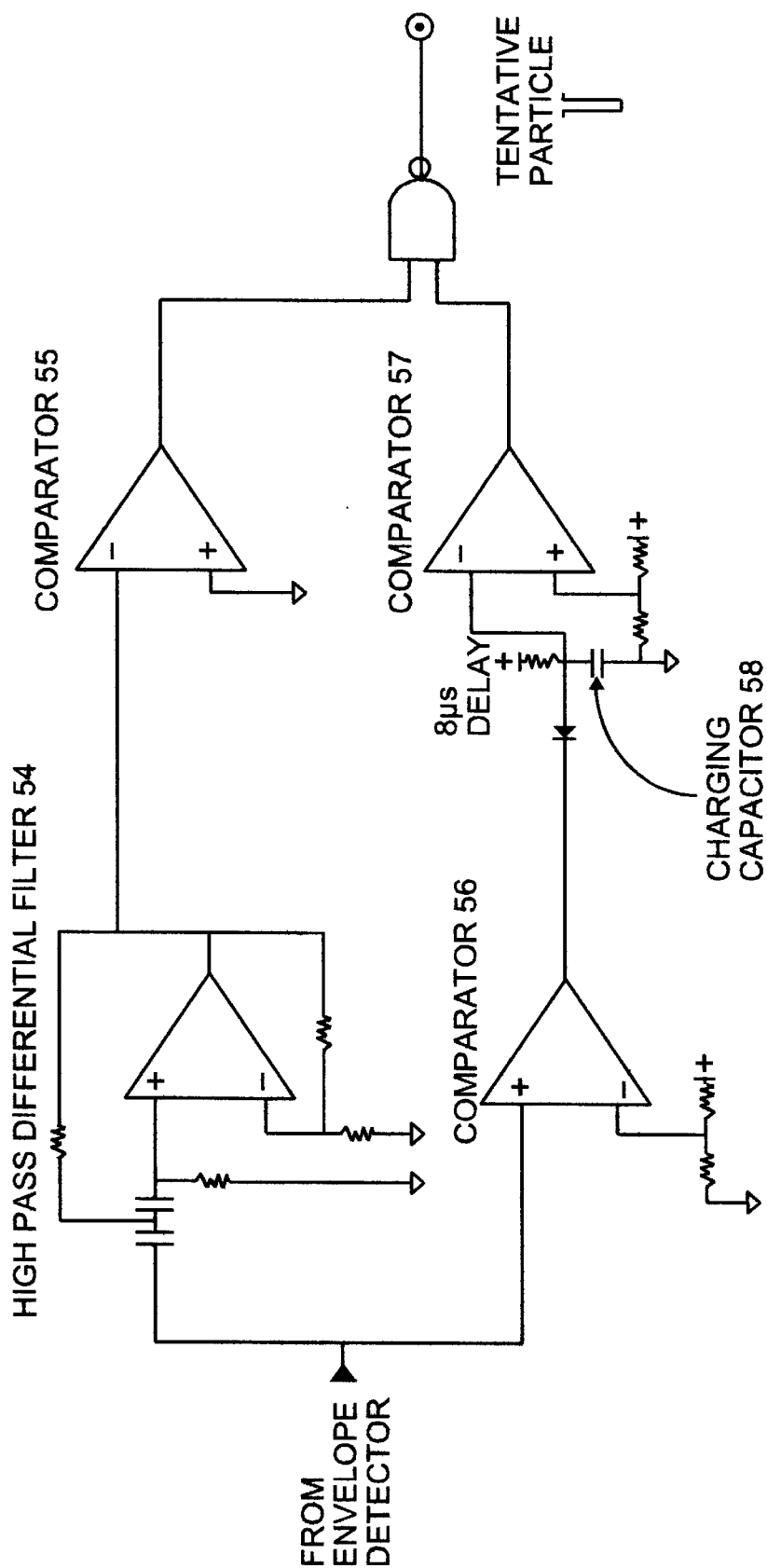
FIG. 11 is a schematic diagram showing details of the blocks in FIG. 9.
Figure 12:
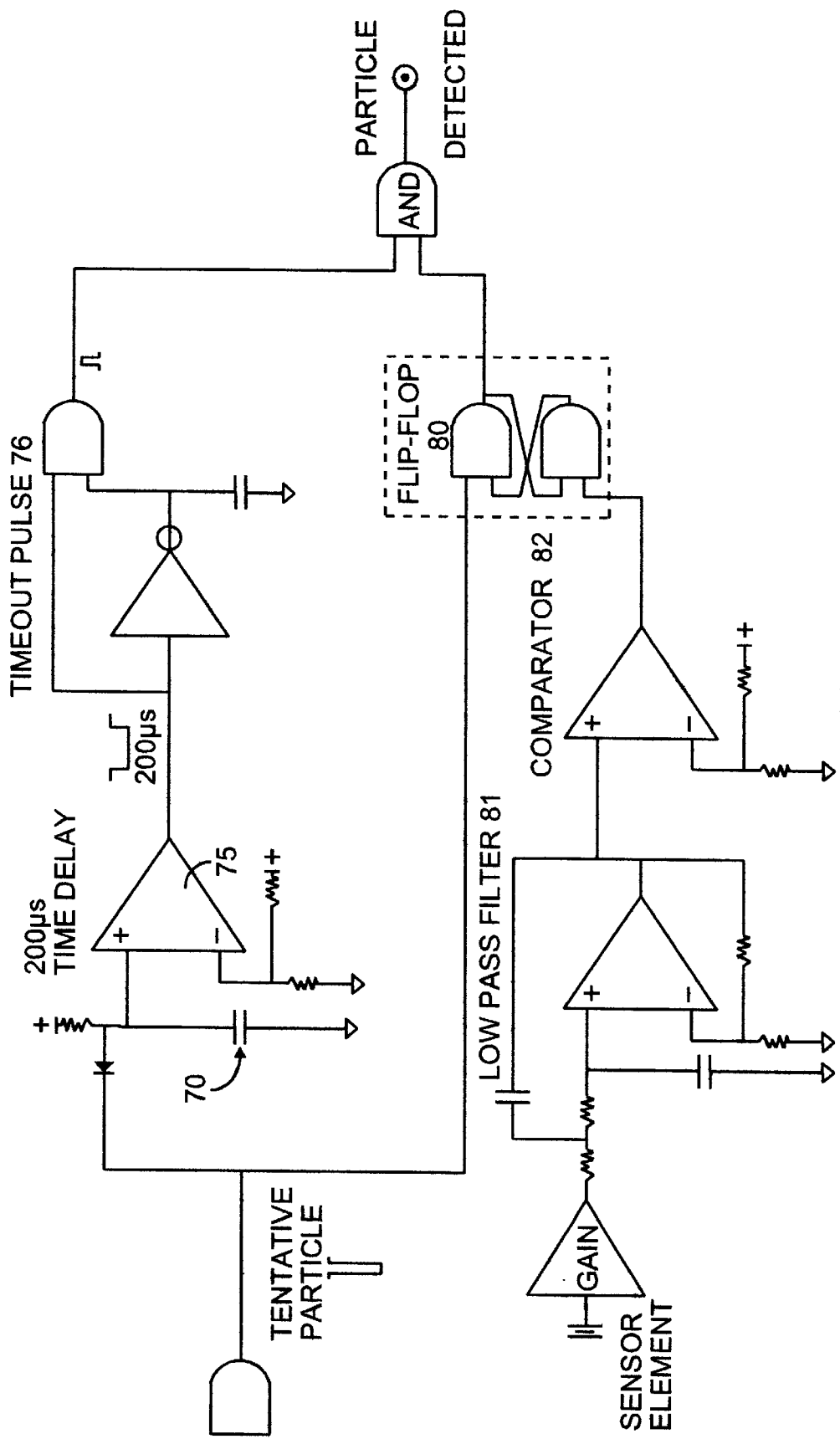
FIG. 12 is a schematic diagram showing details of the blocks in FIG. 9.

Exemplary forms of circuitry which may be used to implement these functions are shown in FIGS. 10, 11 and 12. The subcircuits in these figures comprise well-known signal shaping methods and should be easily appreciated by those skilled in the art. A brief description of the operation of each of these circuits follows:

FIG. 10, shows the Envelope Detector circuitry of FIG. 9. The Envelope Detector is a circuit which forms an approximation to the envelope of the high-frequency component of the piezoelectric sensor signals. Typical outputs from this circuit in response to the waveforms in FIGS. 6, 7 and 8 are sketched as heavy lines respectively in these figures. The circuit includes a high-pass filter 50, a full-wave rectifier 51, a peak follower 52, and finally a low-pass filter 53 to eliminate the original high frequency component.

FIG. 11, shows the Risetime Verify circuitry of FIG. 9. This circuitry operates by detecting the time that its input needs to reach a maximum (peak) value, and comparing that time to an 8 $\mu$s delay. The maximum is the time at which the slope of the input signal first becomes zero. A voltage proportional to the slope of the input is obtained using a differentiator (which is essentially a high-pass filter), so that the moment of zero input slope corresponds to the time at which its derivative passes through zero. Thus the output of a comparator of the differentiator against ground gives the polarity of the slope of the input signal. The circuit includes a high-pass differential filter 54 and three comparators 55, 56, 57.

One method of generating a fixed time delay is to sense the time at which a charging capacitor reaches some preset voltage level. This technique is used twice in this implementation: first in FIG. 11 to generate an 8 $\mu$s delay, and again in FIG. 12 to generate a 200 $\mu$s delay (discussed later herein).

To illustrate, in FIG. 11 the onset of the envelope-detected signal is detected by a comparator 56 biased at a threshold level. While the input is below the threshold the comparator 56 keeps a charging capacitor clamped near ground through a diode. When the input exceeds the threshold the comparator 56 goes positive and allows the voltage of the charging capacitor 58 to rise. Its rate of rise is governed by the well-known RC exponential charging equation. The charging capacitor 58 voltage is applied to another comparator 57, appropriately biased to the voltage that the charging capacitor 58 will reach in 8 μs. Thus, after an 8 μs time delay the comparator 57 output will go from HIGH to LOW.

The 8 μs delay comparator 57 and the slope-detection comparator 58 are combined in a NAND gate. The output of the NAND gate, then, is a signal that is low from the time the slope of the input envelope becomes zero until 8 μs after onset. If the input envelope does not peak within 8 μs, then there is no output from the NAND gate. Hence signals typified by FIG. 7 are ignored. The signal from the NAND gate may be considered a "tentative particle" indication.

FIG. 12 shows the circuitry of the Low Pass Filter, Flip-Flop, and Time Delay blocks of FIG. 9. The circuitry to implement the process of waiting 200 μs after a tentative particle indication while checking for low-frequency components in the sensor signal will now be explained. Note again that a time-delay circuit based on the RC charge curve is employed. The values of the capacitor 70 and associated resistors as well as the comparator 75 bias are selected to give a 200 μs time delay. This timer is initiated by the "tentative particle" pulse from the circuit of FIG. 11. At the end of the 200 μs pulse a short "time out" pulse to formed by timeout pulse circuit 76. This function is implemented here using an inverter and a NAND gate so as to create a logical race condition. The timeout pulse circuit 76 reliably generates a negative pulse on the rising edge of an input signal, during the short time when both inputs to the NAND are HIGH.

The "tentative particle" pulse also sets a bi-stable flip-flop 80. A simple implementation of a bi-stable flip-flop (comprising two cross-connected NAND gates) is shown. As mentioned previously, the output from the piezoelectric sensor is also applied to low-pass filter 81, here implemented by an active-filter Sallen-Key circuit. The output of this filter is applied to a window comparator 82 biased somewhat above the noise level. If there is a low-frequency component in the piezoelectric sensor output then it will pass through the low-pass filter 81 and trigger the comparator 82. This, in turn resets the flip-flop 80. Finally, the 200 μs timeout pulse is ANDed with the flip-flop 80 output. If the flip-flop 80 has not been reset, then the output of the AND gate is an indication that a signal similar to that in FIG. 6 was received.

While the present invention has been described herein with regard to certain preferred embodiments, various modifications could be made without departing from the scope and spirit of the claims appended hereto.

For example, use of the invention is not limited to an internal combustion engine. Lubricants are also used as mechanisms for transmitting power, such as a transmission, a pipe system for oil pressure, such as a hydraulic servo system, industrial rolling, press working, etc. The invention could be used in all of these areas and more to sense particles in fluid.

Additionally, while piezoelectric sensors have been described herein, other types of sensors could also be employed. For example, electromagnetic-induction sensors and electrical capacitance sensors can be used. Further, light emitting diodes and phototransistors can be used to transmit and detect light off of a vibratile portion that makes contact with and is vibrated by particles in the fluid. Changes in the amount of light detected can be indicative of particle contact with the vibratile portion. Still further, the sensor element could take the form of a semiconductor element whose electrical resistance changes as particles make contact therewith.

What is claimed is:

1. A sensor device adapted to detect at least one of a particle and a bubble in a fluid, comprising:
    a sensor element for converting an impact of a particle into an electrical signal, said electrical signal including a high frequency component; and
    a circuit including (i) amplifier means for amplifying the magnitude of the electrical signal, (ii) envelope-detector means for forming an approximation to an envelope of the high frequency component of the electrical signal, (iii) rise-time-verifier means for detecting a rise time of the electrical signal so as to compare the rise time against a first predetermined value, wherein when the rise time is shorter than the first predetermined value, said rise-time-verifier means outputs the electrical signal, and (iv) detecting means for detecting presence of a low-frequency component of said electrical signal during a predetermined time interval, whereby when the low-frequency component is absent, the electrical signal is induced by a particle, and when the low-frequency component is present, the electrical signal is induced by a bubble.

2. A sensor device of claim 1, wherein said detecting means includes a low-pass filter and a flip flop.

3. A sensor device of claim 1, wherein said sensor element includes;
    a diaphragm element having a sufficiently small mass for responding to a collision with a solid particle; and
    an apparatus for converting vibration of said diaphragm element to an electrical signal so as to detect the vibration.

4. A sensor device of claim 1, wherein said sensor element includes:
    a detecting unit including a piezoelectric film consisting essentially of a first ceramic material, a first electrode coated onto at least a portion of the outer surface of said piezoelectric film, and a second electrode coated onto at least a portion of the inner surface of said piezoelectric film; and
    a vibrating portion having a sufficiently small mass for responding to a collision with the solid particle and consisting essentially of a second ceramic material, said detecting unit being placed on said vibrating portion so that said second electrode is coated onto at least a portion of said vibrating portion;
    wherein when one of a solid particle and a bubble in the fluid strikes one of said detecting unit and said vibrating portion, said piezoelectric film converts the vibration into an electrical signal.

5. A method for discriminating an electrical signal induced by a particle in a fluid from an electrical signal induced by a bubble, comprising the steps of:
    detecting a rise time of a high-frequency component of the electrical signal so as to compare the rise time against a first predetermined value; and
    detecting the presence of a low-frequency component of the electrical signal during a second predetermined time period,
    wherein when the low-frequency component is absent then the electrical signal is induced by a particle, and when the low-frequency frequency component is present, then the electrical signal is induced by a bubble.

6. A method of claim 5, wherein said step of detecting a rise time includes a step of forming an approximation to the envelope of the high frequency component of the electrical signal.

7. A method for discriminating an electrical signal induced by a particle in a fluid from an electrical signal induced by a bubble, comprising the steps of detecting the presence of a high-frequency component of an electrical signal during a first predetermined period, detecting the presence of a low-frequency component of an electrical signal during a second predetermined period, wherein when the low-frequency component is absent, then the electrical signal is induced by a particle, and when the low-frequency component is present, then the electrical signal is induced by a bubble.

8. A sensor device adapted to detect at least one of a particle and a bubble in a fluid, comprising (a) a fluid nozzle defining a center of a fluid flow in a first direction; and (b) a plurality of sensor elements arranged in spaced relation in a plane normal to the first direction of fluid flow, a first sensor element being arranged closer to the center of fluid flow than a second sensor element, so that a larger particle tends to strike said first sensor element than the remaining sensor elements, each of said sensor elements being capable of directly converting an impact of one of a particle and a bubble into an electrical signal so that said plurality of sensor elements simultaneously detects particles of different sizes.

9. A sensor device of claim 8, wherein said sensor elements are arranged in a line.

10. A sensor device of claim 8, wherein each of said sensor elements includes:

a diaphragm having a sufficiently small mass for responding to a collision with a solid particle; and an apparatus for converting a vibration of said diaphragm element into an electrical signal so as to detect the vibration.

11. A sensor device of claim 8, wherein each of said sensor elements includes:

a detecting unit including a piezoelectric film consisting essentially of a first ceramic material, a first electrode coated onto at least a portion of the outer surface of said piezoelectric film, and a second electrode coated onto at least a portion of the inner surface of said piezoelectric film; and a vibrating portion having a sufficiently small mass for responding to a collision with a solid particle and consisting essentially of a second ceramic material, said detecting unit being placed on said vibrating portion so that said second electrode is coated onto at least a portion of said vibrating portion;

wherein when one of a solid particle and a bubble in the fluid strikes one of said detecting unit and said vibrating portion, said piezoelectric film converts a resulting vibration into an electrical signal.

12. A sensor device of claim 8, wherein said sensor is adapted to generate electrical signals representative of a plurality of particles, the electrical signals being utilized to calculate average particle size and particle size distribution.

13. A sensor device of claim 8, wherein said sensor is adapted to generate electrical signals representative of a plurality of particles, the electrical signals being utilized to calculate a number of particles larger than a predetermined size.

* * * * *